United States Patent [19]

Deutch et al.

[11] Patent Number: 5,130,250
[45] Date of Patent: Jul. 14, 1992

[54] MOLECULAR CLONING AND EXPRESSION OF NEUTRAL PROTEASE GENES

[75] Inventors: Alan H. Deutch; Victor A. David, both of Columbia, Md.

[73] Assignee: W. R. Grace & Co.-Conn., New York, N.Y.

[21] Appl. No.: 540,035

[22] Filed: Jul. 12, 1990

Related U.S. Application Data

[63] Continuation of Ser. No. 123,038, Nov. 19, 1987, which is a continuation-in-part of Ser. No. 103,983, Oct. 1, 1987, abandoned.

[51] Int. Cl.$^5$ .................. C12N 1/21; C12N 15/00; C12P 21/00; C12P 19/34
[52] U.S. Cl. .................. 435/252.33; 435/68.1; 435/91; 435/172.3; 435/320.1; 435/221; 536/27; 535/350; 935/14; 935/29; 935/38; 935/56; 935/61; 935/73; 935/82

[58] Field of Search .................. 435/68.1, 91, 172.3, 435/320.1, 235, 252.3, 252.33, 221; 536/27; 530/350; 935/9.27, 41, 56, 60, 73

[56] References Cited

FOREIGN PATENT DOCUMENTS 58-162291 of 1984 Japan .

OTHER PUBLICATIONS

Takayi et al. J. Bact vol. 163, pp. 824–831.
Maniatis et al. Molecular Cloning, A laborator Manual Cold Harbor Laboratory CHS, NY (1982) pp. 404–411.

*Primary Examiner*—Joan Ellis
*Attorney, Agent, or Firm*—Vanessa L. Appleby; Jill H. Krafte; Steven T. Trinker

[57] ABSTRACT

Neutral protease genes from *Vibrio proteolyticus* or Bacillus can be cloned and expressed in gram-negative microorganisms, such as *E. coli* or *Serratia*. The functional neutral protease enzyme is expressed.

2 Claims, 8 Drawing Sheets

FIGURE 1A

```
         TTATATATATTGTTAATTAAATATAACGCAATGAATTAATTGTTACTCTATAAATAACATGATTAATTTTATAGAATGTCAACTC
         ---+---------+---------+---------+---------+---------+---------+---------+---------+    100
         AATATATAAACAATTAATTTATATTGCGTTACTTAATTAATTTTTTTTATAACAATGAGATATTTTATTGTACCTAATTAAATATCTTACAGTTGAG i  y  l  l  i  k  y  n  a  m  n  .  l  k  k  i  l  v  y  s  i  k  .  h  g  l  i  l  .  n  v  n  s

TAATTGACGTGGGATATAAATATTTTTCTTACAAACTGGAATGTTACAGAAATGTAATTAATGGTTATTTCGCAGTTATCGGAGAGGGTTTAATTTC
         ---+---------+---------+---------+---------+---------+---------+---------+---------+    200
         ATTAACTGCACCCTATATTTATAAAAGAATGTTTGACCTTACAATGTCTTTACATTAATTACCAATAAAGCGTCAATAGCCTCCCAAATTAAAG n  .  r  g  i  .  n  i  f  l  t  n  w  n  v  t  e  m  .  l  m  v  i  s  r  v  i  a  g  g  f  n  f

TGATTTATCAGTAGTTAAACAACGATTGAAAATAATCTCCAGGATTGAGAAATGAATAAAACACAACGTCACATCAACTGGCTGCTGGTGTTAGCGCGG
         ---+---------+---------+---------+---------+---------+---------+---------+---------+    300
         ACTAAATAGTCATCAATTGTTGCTAACTTTATTTAGAGGTCCTAACTCTTTACTTATTTTGTGTTGCAGTGTAGTTGACCGACGACCACGACAATCGCGCC

.  f  i  s  s  .  t  i  e  n  n  l  q  d  .  e  m  n  k  t  g  r  h  i  n  w  l  l  a  v  s  a  a

CAACTGGCGCTACCGTGCACCGCTGCAGAAATGATGCAGCCTGCTAAACCAGGCTCTTAAAGCTCAGTCACAGAGCGTTGCCCCGGT
         ---+---------+---------+---------+---------+---------+---------+---------+---------+    400
         GTTGACGCGATGGACAGTGGCGACGTCTTTACTAGTTGCATTACTACCGTCGGACGATTTGGTCCGAGAATTTCGAGTCAGTCTCGCAACGGGGCCA t  a  l  p  v  t  a  a  e  m  i  n  v  n  d  g  s  l  l  n  g  a  l  k  a  g  s  q  s  v  a  p  v
```

FIGURE 1B

```
                                                                                                    500
GGAAACCGGATTCAACAAATGAAACGAGTGTTTGCCAAATGCAAAGTCGTTATCAACAAACTCACCACGGTCTACCGGTTTTCAACACC
---:----+----:----+----:----+----:----+----:----+----:----+----:----+----:----+----:----+
CCTTTGGCCTAAGTTGTTTACTTTGCTCAACAAACGTTTACCGTTTCACTTGCAGTAATAGTTGTTGAGTGGTGCCAGATGGCCAAAGTTGTGG e  t  g  f  k  q  m  k  r  v  v  l  p  n  g  k  v  k  v  r  y  g  q  t  h  h  g  l  p  v  f  n  t

600
TCGGTAGTGGCGACTGAATCGAAGTCTGGTAGTAGCCGAAGTGTTCGGTGTGATGGCTCAGGGTATCGCAGACGACGTGTCTACACTGACCGCCATCCGTTG
---:----+----:----+----:----+----:----+----:----+----:----+----:----+----:----+----:----+
AGCCATCACCGCTGACTTAGTTCAGACCATCATCGCTTCACAAGCCACACTACCGAGTCCCATAGCGTCTGCTGCACAGATGTGACTGCGGTAGGCAAC s  v  v  a  t  e  s  k  s  g  s  s  e  v  f  g  v  m  a  g  g  i  a  d  d  v  s  t  l  t  p  s  v  e

700
AGATGAAGCAGGCCATTTCAATTGCTAAATCGGCGTTCCAACAGCAAGAAAAATGTTGCGAACCTGCAACGAAAAGCCGAGTTGATGGT
---:----+----:----+----:----+----:----+----:----+----:----+----:----+----:----+----:----+
TCTACTTCGTCCGGTAAAGTTAACGATTTAGCGCAAGGTTGTCGTTCTTTTTTACCAACGCCCTTGACGTTGCCTTTTGCTCAACTACCA m  k  g  a  i  s  i  a  k  s  r  f  g  q  g  e  k  m  v  a  e  p  a  t  e  n  e  k  a  e  l  m  v

800
TCGTCTCGGACGACAACAATCAAGCCAACTAGTGTATCTGGTTGATTTCTTCGTTGCCGAGATCACCCAGGCCGTCCTTTCTTTTTCATTGATGCCGCAA
---:----+----:----+----:----+----:----+----:----+----:----+----:----+----:----+----:----+
AGCAGACCTGCTGTTGTTAGTTCGCGTTGATCACATAGACCAACTAAAGAAGCAACGCTCCTAGTGGTCGGCCAGGAAAGAAAAGTAACTACGCGTT r  l  d  d  n  n  q  a  q  l  v  y  l  v  d  f  f  v  a  e  d  h  p  a  r  p  f  f  f  i  d  a  q
```

FIGURE 1C

```
                                                                                                           900
ACGGGTGAAGTACTGCAAACTTGGGATGTCTGAACCATGCACAAGTGACGGTACTGGCCCTGGCGTAACACCAAACAGTCGTTATGAATACGGTT
---+----:----+----:----+----:----+----:----+----:----+----:----+----:----+----:----+----:----+----
TGCCCACTTCATGACGTTTGAACCCTACGACTGGTACGTTGACTGTTCGACTGCCATGTGGTTTGTCGCAGCAATACTTATGCCAA
  t  g  e  v  l  q  t  w  d  g  l  n  h  a  q  a  d  g  t  g  p  g  g  n  t  k  t  g  r  y  e  y  g  s

1000
CTGACTTTCCTCCGTTTGTCATCGATAAAGTCGGCACTAAGTGTTCAATGAACAACAGCGGTAAGAACGTTGACCTGAACGCTCAACTTCAGTAA
---+----:----+----:----+----:----+----:----+----:----+----:----+----:----+----:----+----:----+----
GACTGAAAGGAGGCAAACAGTAGCTATTTCAGCCGTGATTCACAAGTTACTTGTTGTCGCCATTCTTGCCAACTGGACTTGCCGAGTTGAAGTCCATT
  d  f  p  p  f  v  i  d  k  v  g  t  k  c  s  m  n  n  s  a  v  r  t  v  d  l  n  g  s  t  s  g  n

1100
CACCACTTACAGCTATACCTGTAACGACTCAACAACTACAAGATTACAAAGCCATTAACGGGCGTACTCGCCACTGAACGATGCCCACTACTTCGGT
---+----:----+----:----+----:----+----:----+----:----+----:----+----:----+----:----+----:----+----
GTGGTGAATGTCGATATGGACATTGCTGAGTTGTTGATGTTTCGGTAATGTTTCGTAATGTTCCGCGACTTGCTACGGGTGACTGATGAAGCCA
  t  t  y  s  y  t  c  n  d  s  t  n  y  n  d  y  k  a  i  n  g  a  y  s  p  l  n  d  a  h  y  f  g

1200
AAAGTGGTTTTCGATATGTACAAAGACTGGATGAACACCACCACTGACGTTCCAGCTGACTTGTTCACTATGCGTGTTCACTATGGTAACAACTACGAAAACGCGT
---+----:----+----:----+----:----+----:----+----:----+----:----+----:----+----:----+----:----+----
TTTCACCAAAGCTATACATGTTTCTGACCTACTGGTGGTGACTGCAAGGTCGACTGATACGCCACAAGTGATACCATTGTTGATGCTTTTGCGCA
  k  v  v  f  d  m  y  k  d  w  m  n  t  t  p  l  t  f  g  l  t  m  r  v  h  y  g  n  n  y  e  n  a  f
```

FIGURE 1D

```
TCTGGAATGGTTCATCCATGACCTTCGGTGATGGCTACAGCACCTTCTACCCGCTGGTGGATATTAACGTTAGTGCCCACGAAGTGAGCCACGGTTTCAC
----+----+----+----+----+----+----+----+----+----+----+----+----+----+----+----+----+----+----+----
AGACCTTACCAAGTAGTAGTGGACTGGAAGCCACTACCGATGTCGTGGAAGATGGGCGACCACCTATAATTGCAATCACGGGTGCTTCACTCGGTGCCAAAGTG
                                                                                                1300
 w  n  g  s  s  m  t  f  g  d  g  y  s  t  f  y  p  l  v  d  i  n  v  s  a  h  e  v  s  h  g  f  t

CGAACAAAACTCGGGTCTCTGGTGTACGAGAATATGTCTGGTGGTATGAACGAAGCGTTCTCTGATATTGCAGGTGAAGCAGCAGAGTTCTACATGAAAGGC
----+----+----+----+----+----+----+----+----+----+----+----+----+----+----+----+----+----+----+----
GCTTGTTTTGAGCCCAGAGACCACATGCTCTTATACAGAGACCTACTTGCTTCGCAAGAGACTATAACGTCCACTTCGTCGTCTCAAGATGTACTTTCCG
                                                                                                1400
 e  q  n  s  g  l  v  y  e  n  m  s  g  g  m  n  e  a  f  s  d  i  a  g  e  a  a  e  f  y  m  k  g

AGCGTTGACTGGGTTGTCGGTGCGGATATCTTCAAATCATCCGGCGGTCTGCGTTACTTTGATCAGCCTTCGCCTGACGCCCTTCTATCGACCATGCGT
----+----+----+----+----+----+----+----+----+----+----+----+----+----+----+----+----+----+----+----
TCGCAACTGACCCAACAGCCACGCCTAGAAGTTTAGTAGGCCGCCAGATGAAACTAGTCGGACGCCACTGCCGGCAAGATAGTCGGTACGCA
                                                                                                1500
 s  v  d  w  v  v  g  a  d  i  f  k  s  s  g  g  l  r  y  f  d  q  p  s  r  d  g  r  s  i  d  h  a  s

CTGACTACTACAATGGCCTGAATGTTCACTACTCAAGTGGTGTATTCAACCGTGCCGTTCTACCTGCTGGCTAACAAAGCGGGTTGGGATGTACGCAAAGG
----+----+----+----+----+----+----+----+----+----+----+----+----+----+----+----+----+----+----+----
GACTGATGATGTTACCGGACTTACAAGTGATGAGTTCACCACACATAAGTTGGCACGCAAGATGACGACCGATTGTTCGCCAACCCTACACTGCGTTTCC
                                                                                                1600
 d  y  y  n  g  l  n  v  h  y  s  s  g  v  f  n  r  a  f  y  l  l  a  n  k  a  g  w  d  v  r  k  g
```

```
TCAGCGCAAGCGGGTACTACGTTATCACGTTATGCTGCGTGGTTACAGCAATTACGCTGCTGTCGTGCTGTAACTTTGCTGTGACTAAACTCAGAATGAACCAGTG
----+----|----+----|----+----|----+----|----+----|----+----|----+----|----+----|----+----|----+----|     2100
AGTCGCGTTCGCCCATGATGCAATACGACGCACCAATGTCGTTAATGCGACCACTGAAACGCACGACGATTGAGTCTTACCTTGGTCAC
 s  a  g  t  t  y  h  v  m  l  r  g  y  s  n  y  a  g  v  t  l  r  a  d  .  t  q  n  g  t  s  e

AAGGCGCACCTTAAGTCGCCCTTTTTTGTATCAGGCGATCTGTGTAAACGTGACCTGATCGAAGTGAGGATTGGCCGCCAGGCGTTGCATGCTGTGTAAG
----+----|----+----|----+----|----+----|----+----|----+----|----+----|----+----|----+----|----+----|     2200
TTCCGCGTGGAATTCCAGCCGGGAAAAAACATAGTCCGTAGACACATTTGCACTGACTAGTTCACTCCTAACCGGCGGTCGCGAACGTACGACACATTC
 g  a  p  .  g  r  l  f  c  i  r  r  s  v  .  t  .  p  d  r  s  e  d  w  p  p  a  l  a  c  c  v  r

GACTCGGTGGGCAACGTCTCATGGCCACTGATGTCGCAATGACGATGGCCCTCTTTTCGTTCTGTGGTGTATGTTGTATCGACCGCGTCCCTTCCACAA
----+----|----+----|----+----|----+----|----+----|----+----|----+----|----+----|----+----|----+----|     2300
CTGAGCCACCCGTTGCAGAGTACCGGTGACTACTGCTACCGGTACTGCTACCGGAGAAAAGCAAGACACCACATACAACATAGCTGGCGGCAGGGAAGTGTT
 t  r  w  a  t  s  h  g  h  w  m  s  q  .  r  w  p  l  f  v  l  w  c  m  l  y  r  p  p  s  l  p  q

TCGTGCCGTTGAGCAGTTTGAGTCTGACTGGCAGGTGATAAAGGCAGGCAATCTCGATGTAATCGTACTGGCTGCAG
----+----|----+----|----+----|----+----|----+----|----+----|----+----|-----        2377
AGCACGGCAACTCGTCAAACTCAGACTGACCGTCCACTACTGTTCCGTCCGTTAGAGCTACATTAGCCATGACCGACGTC
 s  c  r  .  a  v  .  v  .  l  a  g  d  k  g  r  g  s  r  c  n  r  t  g  c  s
```

MOLECULAR CLONING AND EXPRESSION OF NEUTRAL PROTEASE GENES

This is a continuation-in-part of U.S. Ser. No. 103,983, now abandoned entitled "Molecular Cloning and Expression of Protease Genes" (A. H. Deutch and V. A. David), filed Oct. 1, 1987.

This is a continuation of application Ser. No. 123,038, filed Nov. 19, 1987.

BACKGROUND OF THE INVENTION

This invention relates to the isolation and cloning of neutral protease genes and the expression of the cloned genes in gram negative bacteria. More specifically, genes coding for neutral proteases have been cloned and expressed, with confirmation that the clones synthesize and secrete active neutral protease enzyme.

*Vibrio proteolyticus* (*Aeromonas proteolytica*), which contains in its genome one or more genes for neutral protease, has been identified and cultured. Griffin et al., "Some Physical Characteristics of a Proteinase from Aeromonas proteolytica," J. Biol. Chem., Vol. 245, pp. 1348–56 (1970), describes a proteinase isolated from culture filtrates of *A. proteolytica*. Bayliss et al., Archives of Biochemistry and Biophysics, 204:214–219, (1980), isolated and identified a neutral protease from *Aeromonas proteolytica*. Neutral proteases also have been prepared by cultivating various *Bacillus* strains, as taught in U.S. Pat. No. 3,796,635 (Delente).

Purification of enzymes for industrial uses is hampered by the typically low levels of enzyme produced by naturally occurring isolates. Using genetic engineering to manipulate the gene coding for an enzyme of interest, the gene can be relocated into other organisms for both laboratory development and industrial production of the enzyme. Drawbacks associated with production of the enzyme in its natural environment can thereby be avoided.

Previous attempts at cloning related protease enzymes in *E. coli* have yielded varying results. For example, Yanagida et al., "Specific Excretion of *Serratia marcescens* Protease through the Outer Membrane of Escherichia coli," J. Bacteriology, 166:937–44 (1986), discloses cloning of a serine protease DNA fragment from the microorganism *Serratia marcescens* into *E. coli* in which there was specific secretion of the protease into the extracellular medium. By contrast, Nakahama et al., "Cloning and Sequencing of *Serratia* Protease Gene," Nucleic Acids Research, 14:5843–55 (1986), found no excretion upon cloning the Serratia sp. E-15 extracellular metalloproteinase gene into *E. coli*, but reported excretion of the protease into the culture medium when the gene was cloned back into *Serratia*.

SUMMARY OF THE INVENTION

In the present invention, neutral protease genes are cloned and expressed in gram-negative microorganisms. The expression products in the host have been identified as active, functional neutral protease enzymes.

It is a primary purpose of this invention to isolate neutral protease genes from the genomes of microorganisms known to carry them, and to relocate the genes in a gram-negative host, such as *E. coli*, in which the genes are expressed. A related object is to locate the genes in hosts which will synthesize the active neutral protease enzyme.

Still another object is to provide the neutral protease gene in a form in which it may be readily manipulated for further study and development. The isolated neutral protease gene can more readily be associated with more powerful promoters, altered by site-directed mutagenesis, etc. Locating the gene in a well-characterized host, such as *E. coli*, will greatly facilitate the desired genetic manipulations.

It is an additional object of this invention to provide a novel method for the production of neutral protease enzymes, in particular for production of the mature enzymes. That is, it is intended that this invention make possible the expression of neutral protease genes outside their natural environment.

BRIEF DESCRIPTION OF THE DRAWINGS

Figure 1E:
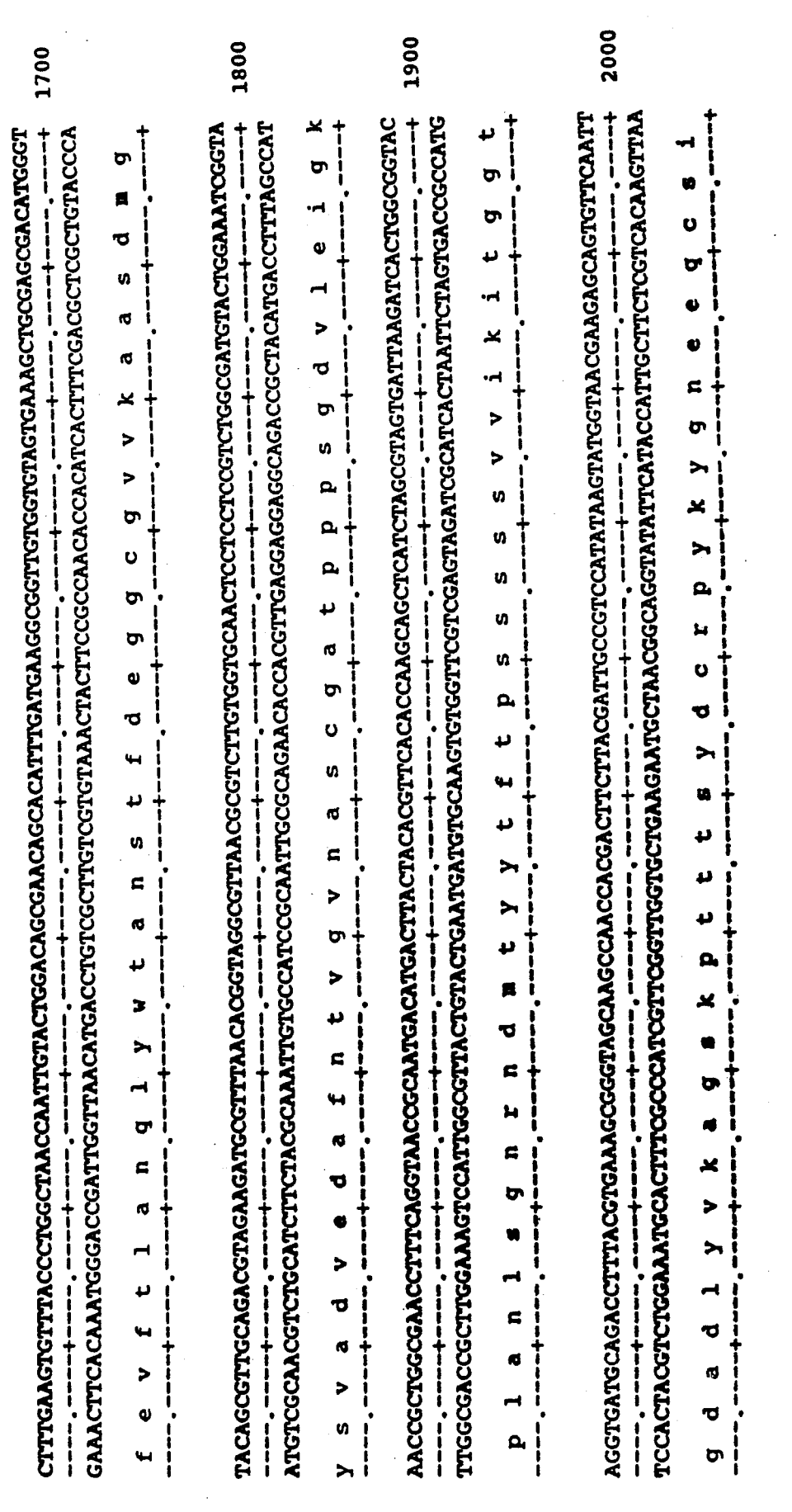

FIG. 1 (2 pages) is a representation of the DNA sequence of the extracellular neutral protease (vibriolysin) gene from *Vibrio proteolyticus* ATCC 53559.

DETAILED DESCRIPTION OF THE INVENTION

Figure 2:
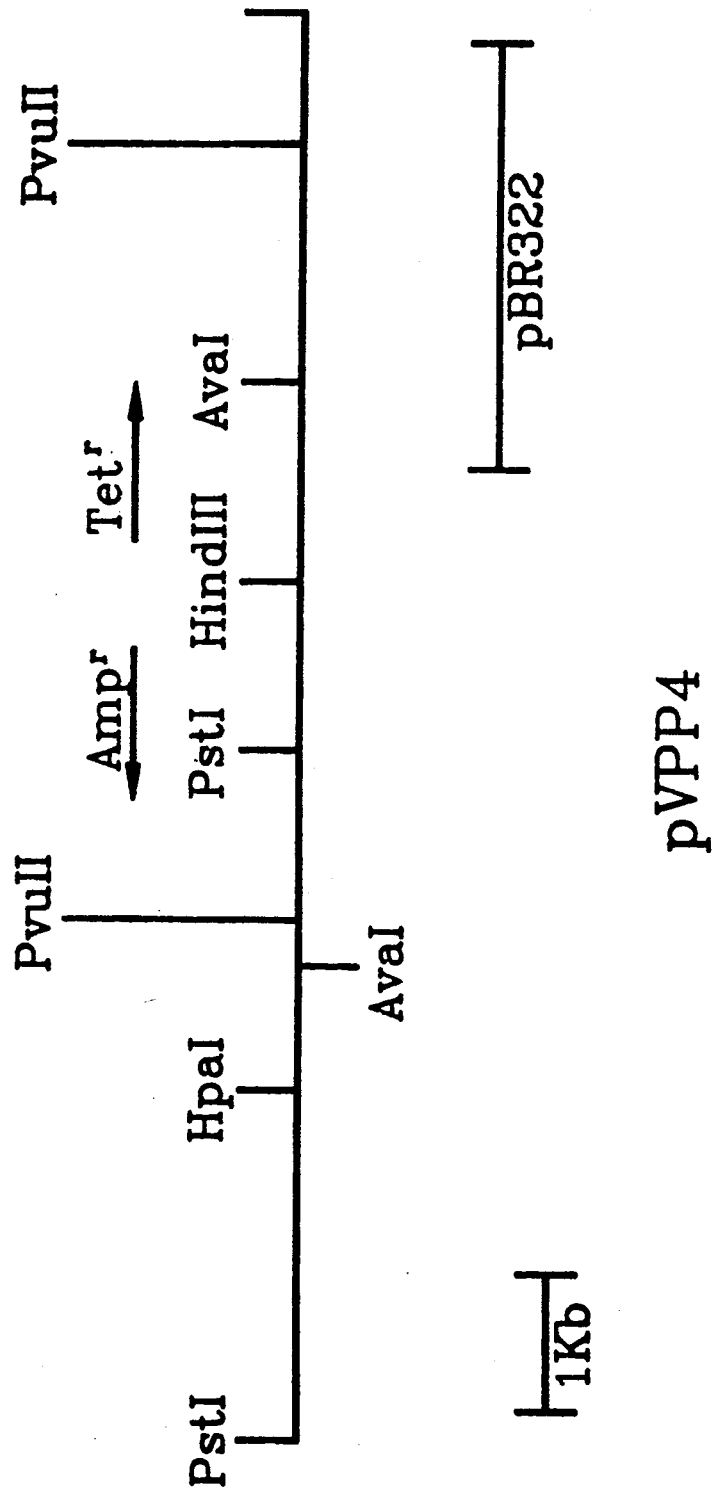
FIG. 2 is a restriction map of the plasmid pVPP4 of Example II, with a Pst I fragment containing a portion of the Vibrio neutral protease gene.

Cloning and expression of neutral protease genes form the basis of the present invention. The desired gene is isolated, ligated into an appropriate vector, and cloned into a gram-negative bacterium, the first time such a host has been used for expression of foreign neutral protease enzymes from *Vibrio* and *Bacillus*. In the Examples described below, the gram-negative host was *E. coli*. The protease enzyme is synthesized in the active enzyme form. Moreover, it has been found that the enzyme is either secreted from the bacterial host or is released upon lysis of the host cell.

In this description, the terms "active" or "functional" are used to describe the expressed neutral protease prepared according to this invention. This contrasts with the pre-pro-enzyme, which is not believed to be an active enzymatic composition. The enzyme is determined to be in the active form by one of the assays described below, for example, the milk-clearing assay.

The neutral protease genes cloned by the present invention are isolated from *Vibrio proteolyticus* (*Ameromonas proteolytica*) or Bacillus strains, including *Bacrllus stearothermophilus*, *Bacillus subtillis* and *Bacillus thermoproteolyticus*, which are all known to produce neutral protease enzymes. Specific strains have been identified in the literature, but this invention is not intended to be limited to specific Vibrio proteolyticus or Bacillus strains, so long as the strain harbors one or more neutral protease genes. Bacillus strains are widely available from culture collections and one would expect that most Bacillus strains will contain appropriate neutral protease gene(s), except strains known to be or to have been made protease-negative. Similarly, Vibrio strains are available, for example, *Vibrio proteolyticus* ATCC 53559 is available from the American Type Culture Collection, 12301 Parklawn Drive, Rockville, MD 20852, and is known to contain one or more neutral protease genes.

According to the present invention, a gene library is prepared, using the DNA of the source cells (the Vibrio or Bacillus cells as described above), which have been determined to synthesize neutral protease enzyme. Assays for the presence of neutral protease enzyme(s) are known to the art and are described below. Chromosomal DNA is extracted from the source cells and digested with restriction enzyme(s) by known procedures to give cleavage of the DNA into large fragments. Partial digestion with Sau 3A is preferred although other restriction enzymes (e.g., Mbo 1, Bam H1, etc.) may be used. The precise procedures and techniques used for the construction of a gene library are well known and need not be described here in detail, although additional detail is given in the Examples.

The DNA fragments are ligated into vectors suitable for allowing isolation of clones which express the neutral protease enzyme. In the preferred embodiment of this invention, the cosmid vector pHC79 is used, following cleavage with Bam H1 restriction enzyme. The recombinant vectors (in this embodiment, pHC79 cosmids containing DNA fragments from the neutral protease-containing genome) are then packaged into bacteriophage particles, preferably bacteriophage lambda, thereby producing a gene library in bacteriophage lambda particles. For production of a gene library in bacteriophage, a cosmid vector or lambda vector is used. In other cases, plasmid vectors may be used. The precise method for inserting the genes into the host cells is not critical and any of the methods practiced in the art will be suitable.

The recombinant bacteriophage particles are thus used to insert the DNA fragments into the desired gram-negative host cells. In the preferred embodiment, the recombinant bacteriophage particles are used to transfect E. coli. In the Examples which follow, use of the strain E. coli HB101 is described, but other strains of E. coli may be used if desired. Since E. coli strains do not naturally synthesize an extracellular neutral protease enzyme, the E. coli clones easily may be evaluated for the presence and expression of the neutral protease gene by the assays described below, particularly the milk-clearing assay.

There are a number of standard assays which may be used to determine whether the neutral protease gene is being expressed. For example, confirmation by PAGE analysis may be made, using a sample of purified neutral protease enzyme for comparison. Alternatively, the recombinant clones containing the neutral protease gene may be identified by their ability to produce a zone of clearing on milk agar plates. It is known that colonies of Vibrio or Bacillus which synthesize neutral protease will produce such a zone. Non-recombinant E. coli colonies do not, nor do other hosts which do not secrete a protease naturally. Clones of this invention which contain the neutral protease gene are therefore readily identified by this assay. This milk-clearing assay is preferred for use with E. coli and other host strains which do not naturally produce an extracellular neutral protease. Other gram-negative strains may be used as hosts. For example, Serratia clones may be prepared, although evaluation for the presence and expression of the Vibrio or Bacillus neutral protease gene will be somewhat more complex, since Serratia may be expected to naturally clear milk due to secretion of its own neutral protease. For Serratia, the FAAPA assay described below or any quantitative enzymatic assay may be used. Of course, where neutral protease-negative strains of Serratia are used, the qualitative milk-clearing assay will be suitable.

Confirmation may be made by using other protease assays. For example, clones may be confirmed for expression of the protease enzyme by demonstrating that the fermentation broths of those clones are capable of hydrolyzing substrates such as Hide powder azure, azocoll or N-[3-(2-furyl)acryloyl]-L-alanyl-phenylalaninamide (FAAPA). Alternatively, these assays may be used in the first instance to identify the neutral protease gene-containing clones.

It is significant in two respects that expression of the neutral protease gene in E. coli and other "non-secreting" hosts (that is, hosts which do not naturally secrete a neutral protease) can be detected as a zone of clearing on a milk agar plate. First, this is evidence that the active, functional enzyme is being synthesized by the gram-negative host. Second, the extracellular presence of neutral protease on the milk agar plates is evidence that the enzyme is being externalized in some manner, either by secretion or by cell lysis. Since E. coli and some other gram-negative bacteria normally do not secrete significant quantities of proteases into the media, this is important in terms of the ability to recover neutral protease enzymes produced as a result of expression of the V. proteolyticus or Bacillus neutral protease genes in these nonsecreting hosts.

The recombinant gram-negative clones containing the foreign neutral protease gene(s) can be used in a variety of ways. As previously mentioned, these clones have great value as research and development tools. The neutral protease genes are particularly easily manipulated in E. coli. In this form, the genes more readily can be associated with powerful promoters and the like, for the overproduction of the neutral protease enzyme. Site-directed mutagenesis also is possible.

In addition to using the clones of this invention to facilitate laboratory manipulation of the gene(s), this invention offers an alternative means for the production of the enzyme itself. Production of the Vibrio or Bacillus neutral protease enzyme in a gram-negative microorganism is unique to this invention. Since the active enzyme is produced, no further operations or manipulations are required to yield the functional neutral protease.

The Examples which follow are given for illustrative purposes and are not meant to limit the invention described herein. The following abbreviations have been used throughout in describing the invention:

| | |
|---|---|
| °C. - | degrees Centigrade |
| DNA - | deoxyribonucleic acid |
| gm - | gram(s) |
| kb - | kilobase |
| M - | mole(s); molar |
| mg - | milligram(s) |
| ml - | milliliter(s) |
| mM - | millimole(s); millimolar |
| μgm - | microgram(s) |
| μl - | microliter |
| min - | minute(s) |
| N - | normal |
| OD - | optical density |
| rpm - | revolutions per minute |
| SDS - | sodium dodecyl sulfate |
| PAGE - | polyacrylamide gel electrophoresis |

EXAMPLE I

(Cloning of *Vibrio proteolyticus* Neutral Protease)

A. Preparation of Chromosomal DNA — Chromosomal DNA was prepared as described by Hull et al. (Infection and Immunity, 33:933-938 (1981)). *Vibrio proteolyticus* ATCC 53559 was obtained. A viable culture of this strain has been irrevocably deposited with the American Type Culture Collection (ATCC), 12301 Parklawn Drive, Rockville, MD 20852. All restrictions on the availability of this strain to the public will be irrevocably removed upon the granting of a patent of which this strain is a subject. The culture was incubated at 26° C. with mild agitation in media containing per liter: 20 gm Polypeptone (TM) peptone (BBL Microbiology Systems), 20 gm sea salts (Aquarium Systems), 0.4 gm $MgSO_4$ and adjusted to pH 8.3 with 10N NaOH. The culture was harvested at 18 hours after having reached an optical density (at 640 nanometers) of 8.2. The cells were harvested by centrifugation for 5 minutes at 10,000 rpm. The cells were resuspended in 25 ml of TES (50mM Tris pH 8.0, 5mM EDTA, 50mM NaCl) and then harvested as before. The cells were resuspended in 1.6 ml of TE/sucrose (25% sucrose 50mM Tris pH 8.0, 1mM EDTA) and transferred to a $1 \times 3\frac{1}{2}$ inch Beckman ultracentrifuge tube. Then 0.4 ml of a solution of TE/sucrose containing 100 mg lysozyme (Sigma) was added and the tube was transferred to an ice bath for 15 minutes. Next, 10 $\mu$l of a solution of 20 mg/ml proteinase K (Bethesda Research Laboratories) in TE/sucrose was added, followed by an additional incubation for 15 minutes on ice. At this point, 0.4 ml of 0.5M EDTA and 0.25 ml of a 10% solution of N-lauroylsarcosine were added and the tube was capped with Parafilm "M" (TM) laboratory film (American Can Co.) and incubated 18 hours at 65° C.

Following this incubation, 33 ml of TES containing 50 mg/ml phenyl methyl sulfonyl fluoride (PMSF) (Calbiochem) and CsCl in a ratio of 1.26 gm CsCl to 1.0 ml TES/PMSF was carefully added. The tube was then filled to the top with paraffin oil, sealed and centrifuged for 20 hours at 40,000 rpm at 15° C. Following centrifugation, the top of the tube was vented with a 16-gauge needle and fractions were collected from a 16-gauge needle inserted at the bottom of the tube. The viscous fractions containing chromosomal DNA were dialyzed at 4° C. against four changes of 2 liters of TE (10mM Tris pH 8.0, 1 mM EDTA) over a period of 48 hours. The DNA recovered following dialysis was found to be at a concentration of 380 $\mu$gm/ml based on optical density measurements (at 260 nanometers).

B. Cloning of the Neutral Protease Gene — Cloning of the neutral protease gene of V. proteolyticus was accomplished by the technique of cosmid cloning using the chromosomal DNA isolated from *V. proteolyticus* in Step A of this example. Optimal conditions were determined for digestion with the restriction enzyme Sau 3A to give fragments suitable for cosmid cloning.

Trial digestions were carried out at 22° C. in a total volume of 28 $\mu$l containing 8.9 $\mu$gm chromosomal DNA isolated in Example I, 0.8 units of Sau 3A (Bethesda Research Laboratories), 6mM Tris pH 7.5, 6mM $MgCl_2$, 50mM NaCl and 10 $\mu$gm/ml bovine serum albumin. The reactions were stopped at time points ranging from 0-60 minutes by addition of 1 ul of 0.5 M EDTA and heating for 10 minutes at 70° C. Aliquots from each time point were then analyzed by electrophoresis on a 0.4% agarose gel in TAE (40mM Tris-acetate, 2mM EDTA). After staining the gel with ethidium bromide, the DNA was visualized by illumination with ultraviolet light. The 60 minute time point was chosen as the condition which gave the most DNA in the size fraction between 33–45 kb, which can be packaged into bacteriophage lambda particles.

In order to obtain sufficient DNA for cosmid cloning, the reaction was scaled up. Five tubes identical to the trial digestion were set up and the reaction was stopped at 60 minutes. The five samples were pooled and the chromosomal DNA was dephosphorylated by addition of two units of calf alkaline phosphatase (Bethesda Research Laboratories) and incubated at 37° C for 10 minutes. This was followed by inactivation of the phosphatase by incubation for 10 minutes at 70° C. The sample was then extracted with an equal volume of a mixture containing a 1:1 ratio of phenol:choloroform. (The phenol contained 0.1% 8-hydroxyquinoline and had been equilibrated with 0.1M Tris pH 8.0; the chloroform contained 4% isoamyl alcohol.) The dephosphorylated chromosomal DNA was then precipitated by the addition of one volume of 4M ammonium acetate followed by two volumes of ethanol and incubation for 10 minutes in a dry ice-ethanol bath. The DNA was recovered by centrifugation and washed with cold 70% ethanol. The DNA pellet was dried briefly under vacuum and resuspended in 5 $\mu$l of TE.

The *E. coli* cosmid vector pHC79 (Hohn, B. and Collins, J., Gene, 11:291 (1980)) was prepared for ligation to the Sau 3A partially digested, dephosphorylated chromosomal DNA of *V. proteolyticus* as follows. First, 10 $\mu$gm of pHC79 (Bethesda Research Laboratories) was digested to completion with 5 units of Bam Hl (Bethesda Research Laboratories) in a total volume of 30 $\mu$l using the digestion buffer supplied with the enzyme. The restriction enzyme was inactivated as described for Sau 3A and the sample was phenol/chloroform extracted, ethanol precipitated and resuspended in a total volume of 25 $\mu$l of TE.

The ligation reaction consisted of 4 $\mu$l of Bam Hl digested pHC79, 4 $\mu$l of the Sau 3A digested, dephosphorylated *V. proteolyticus* chromosomal DNA, 0.5 units of T4 DNA ligase (Bethesda Research Laboratories) and 2 $\mu$l of a 5X ligation buffer stock (Bethesda Research Laboratories). After 15 hours at 10° C., 4 $\mu$l of the sample was packaged into bacteriophage particles using an in vitro packaging extract (Giga Pack Gold, Strategene Cloning Systems). The final volume of the packaged DNA sample was 500 $\mu$l. Recipient cells of *E. coli* HB101 (Bethesda Research Laboratories) were prepared by growing overnight at 37° C. with shaking in 20 ml YET-maltose (per liter: 5 gm Bacto-yeast extract (Difco), 5 gm NaCl, 10 gm Bacto-Tryptone (Difco), 5 gm maltose). Then 0.1 ml of this culture was inoculated into 20 ml of fresh YET-maltose and incubated until it reached an optical density (at 640 nanometers) of 1.0. The cells were harvested by centrifugation and resuspended in 10 ml of lambda diluent (per liter: 5.8 gm NaCl, 2 gm $MgSO_4.7H_2O$, 50 ml 1M Tris (pH 7.5), 5 ml 2% gelatin).

A 100 $\mu$l aliquot of HB101 was incubated for 10 minutes at 37° C. with 10 $\mu$l of the packaged DNA sample. Then 1.0 ml of prewarmed YET broth was added and the sample was incubated for 30 minutes at 37° C. The cells were pelleted by centrifugation for 1 minute in a micro-centrifuge, resuspended in 0.1 ml of YET and plated onto a YET agar plate containing 50 $\mu$gm/ml ampicillin and 1% Bacto-skim milk (Difco). The cosmid pHC79 contains a gene which confers resistance to ampicillin. The addition of ampicillin to the media prevents growth of bacteria which do not contain the cosmid. The plates were incubated for 48 hours at 37° C. and then colonies surrounded by zones of clearing were selected for further analysis. The ability of these strains to produce zones of clearing on skim-milk plates was shown to be plasmid determined by isolating plasmid from these strains as described by Maniatis et al. (*Molecular Cloning*, (1982) Cold Spring Harbor Laboratory), transforming the plasmids back into competent HB101, and demonstrating that ampicillin resistant transformants were again capable of producing zone of clearing on skim-milk agar plates.

C. Screening of the Cosmid Clones for Neutral Protease Activity — The neutral protease from *V. proteolyticus* has been shown to be capable of hydrolyzing the synthetic peptide FAAPA (N-[3-(2-furyl)acryloyl]-L-alanyl-L-phenylalaninamide) (Bayliss et al., Archives of Biochemistry and Biophysics, 204:214–219, (1980)). In order to further characterize the protease produced by the cosmid clones of Example II, nine separate isolates which produced zones of clearing on skim-milk agar plates were selected. These isolates, along with HB101 (pHC79) as a control, were incubated at 37° C. with shaking in 10 ml YET broth containing 50 μgm/ml ampicillin in a 15 ml tube for 60 hours. The cells were removed by centrifugation and the broth was concentrated 10-fold by centrifugation for several hours at 4° C., 5000 rpm.

The concentrated samples were then used in enzyme assays using FAAPA (Sigma Chemical Co.) as the substrate. A 20 μl aliquot of the concentrated broth was added to 500 μl of a solution containing 0.5 mM FAAPA, 0.01 M HEPES pH 7.2, and 0.01 M $CaCl_2$. The samples were incubated at room temperature and the hydrolysis of FAAPA was observed by spectrophotometry (at 335 nanometers) as a decrease in optical density. Broth from all nine cosmid clones (and V. proteolyticus grown as described in Example I for the chromosomal DNA preparation) were shown to contain FAAPA-hydrolyzing activity, while broth from the control HB101 (pHC79) had no such activity.

For further confirmation that the *E. coli* cosmid clones were producing *V. proteolyticus* neutral protease, the mobility of the *E. coli* product was compared to that of purified neutral protease by native polyacrylamide gel electrophoresis (PAGE). Neutral protease purified from *V. proteolyticus* as described by Griffen et al. (Journal of Biological Chemistry, 254:1348 (1970)) gave a single band when subjected to PAGE and staining on a Pharmacia Phast System (TM) (Pharmacia) gel apparatus. When an unstained gel was overlaid with a molten solution containing 10% Bacto-skim milk, 0.7% agarose, and 0.01 M HEPES buffer pH 7.2 and incubated several hours at 37° C., a zone of clearing was produced at the same $R_f$ as the single band present in the stained gel, confirming the identity of that band. The concentrated broth of one of the cosmid clones of Example II was electrophoresed on the same gel as the purified neutral protease and concentrated HB101(pHC79) broth. The gel was overlaid with a skim-milk agarose solution following electrophoresis. It was shown following electrophoresis that the broth from the cosmid clone, but not HB101 (pHC79), produced a zone of clearing in the overlay at the same position as that produced by the purified neutral protease from *V. proteolyticus*.

EXAMPLE II

Subcloning of the Vibrio Neutral Protease Gene

Figure 3:
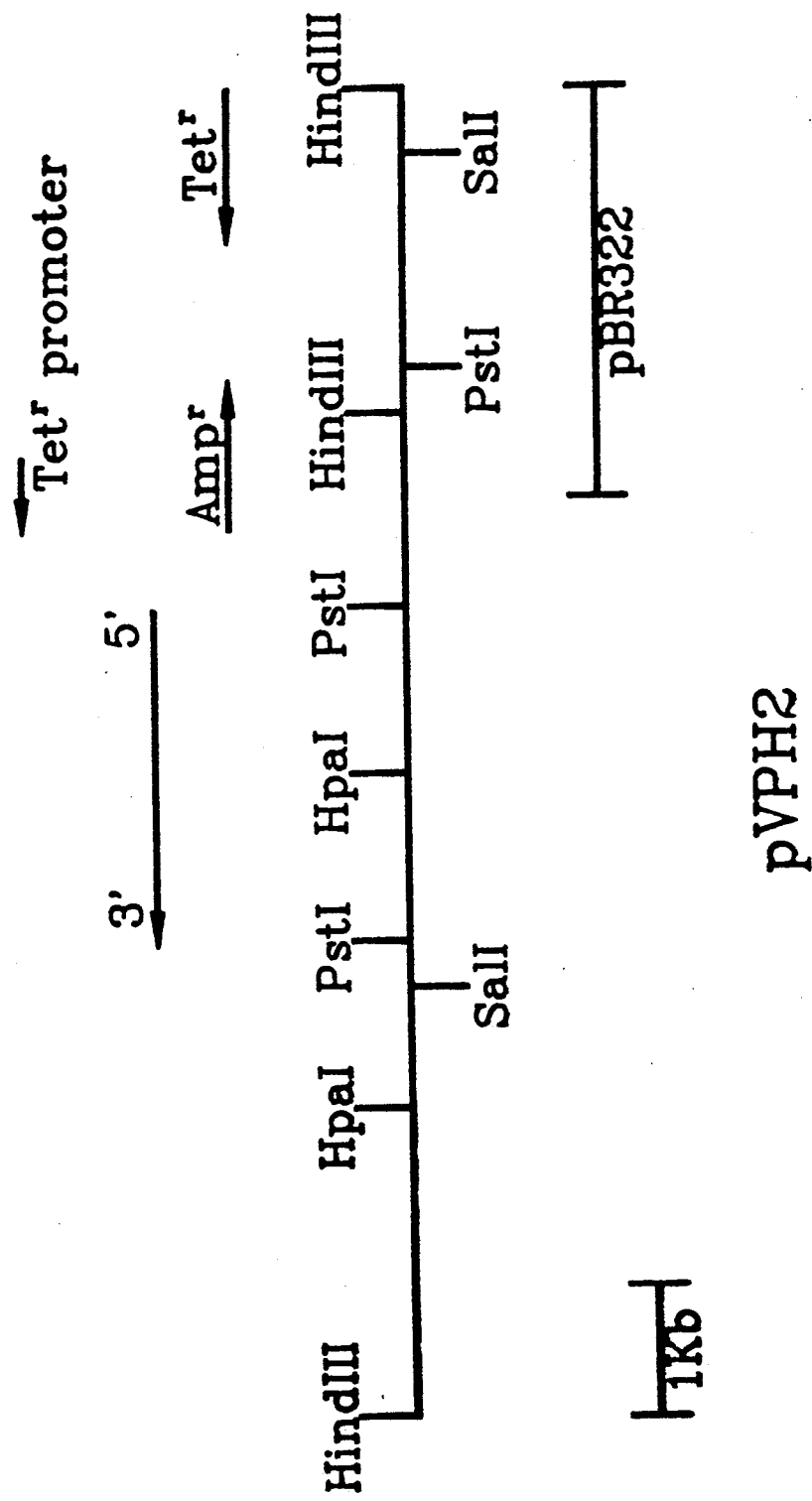
FIG. 3 is a restriction map of the plasmid pVPH2 of Example II, with a Hind III fragment containing the Vibrio neutral protease gene.

For further genetic characterization of the neutral protease gene, it was convenient to remove the gene from the large cosmid clone onto a smaller plasmid. A cosmid (designated pVP8) was selected from those prepared in Example I as the source of material for subcloning in this Example. This cosmid was isolated from a clone designated HB101 /pVP8 using a standard alkaline lysis technique. A viable culture of this recombinant clone has been irrevocably deposited with the American Type Culture Collection (ATCC), 2301 Parklawn Drive, Rockville, MD 20852, and was given the accession number ATCC 67501. All restrictions on the availability of this strain to the public will be irrevocably removed upon the granting of a patent of which this strain is a subject. Cosmid pVP8 was digested with the restriction enzymes Pst I or Hind III. The restriction fragments were ligated respectively to the Pst I or Hind III digested, 5' dephosphorylated vector pBR322. The ligated material was transformed into HB101 using standard techniques, and the cells were plated on YET-Skim Milk plates containing 50 μgm/ml ampicillin (Hind III) or 12.5 μgm/ml tetracycline (Pst I). The clones containing the neutral protease gene were identified by the formation of zones of clearing surrounding them. Plasmids were isolated from these clones and restriction enzyme maps of them were prepared. A 6.7 kb Hind III fragment on a plasmid designated pVPH2 contains the entire open-reading-frame encoding the Vibrio neutral protease (FIG. 3). A 2.1 kb Pst I fragment on a plasmid designated pVPP4 contains a portion of the gene encoding the *Vibrio* neutral protease (FIG. 2). A viable culture of the plasmid pVPH2, in the host *E. coli* HB101, has been irrevocably deposited with ATCC and given accession number ATCC 67499. All restrictions on the availability of this strain to the public will be irrevocably removed upon the granting of a patent of which this strain is a subject. The restriction maps of the two plasmids are shown in FIGS. 2 and 3, respectively: The strain *E. coli* HB101/pVPH2 (ATCC 67499) was shown to be capable of synthesizing the neutral protease of *Vibrio proteolyticus*. This was deduced following enzymatic assays and protein gel analysis of culture supernatants in which this strain wa grown conducted as follows.

A. Preparations of Culture Broths — The strain HB101/pVPH2 (containing the recombinant plasmid believed to express the Vibrio neutral protease gene) along with the appropriate controls HB101/pBR322 (containing the non-recombinant plasmid) and *Vibrio proteolyticus* were inoculated from overnight cultures grown in Luria broth into 50 ml fresh Luria broth in a 250 ml shake flask. For HB101/pVPH2 and HB101/pBR322, the media contained 50 μgm/ml ampicillin. The cultures were incubated at 37° C. with shaking at 200 rpm for 16 hours. All the cultures grew to an $OD_{640}$ of approximately 2.0. The cells were removed from the broth by centrifugation and 2.0 ml of the broths were concentrated in Centricon 10 (TM) miniconcentrators (Amicon Division, W. R. Grace & Co.) then washed with 50 mM Tris (pH 7.4) to remove salts and low molecular weight peptides. The broths of HB101/pVPH2 and HB101/pBR322 were concentrated 35-fold and the broth of *Vibrio proteolyticus* was concentrated 4-fold prior to enzyme assay.

B. FAAPA Enzyme Assay — The concentrated broths were assayed for their ability to hydrolyze the synthetic peptide FAAPA as in Example I. Reaction conditions were 0.5 mM FAAPA, 50 mM Tris (pH 7.4), 25° C. and hydrolysis of FAAPA was monitored at $OD_{335}$ in a Beckman model 25 spectrophotometer. Standard curves were constructed using 1-6 μl of the 4-fold concentrated broth from *Vibrio proteolyticus*, which gave a linear rate response with respect to enzyme concentration. Appropriate amounts of broths from *E. coli* were added so that rates fell within this range. The results of this experiment are shown in Table I. The *E. coli* HB101 carrying the recombinant plasmid pVPH2 (HB101/pVPH2) encodes a gene responsible for FAAPA hydrolysis; the control organism HB101/pBR322 does not.

TABLE I

| Sample | Enzyme Present[1, 2] |
|---|---|
| HB101/pVPH2 | 32.0 units/ml |
| HB101/pBR322 | 0.2 units/ml |
| *V. proteolyticus* | 1400.0 units/ml |

[1]One unit is defined as the amount of enzyme required to cause a change of 0.001 OD units per minute under the reactive conditions employed.
[2]Units/ml are expressed for the activity which would be present in unconcentrated broth.

C. Detection of Vibrio neutral protease activity following PAGE assay — Analysis by PAGE was carried out with the concentrated culture broths on a Pharmacia Phast System (TM) (Pharmacia). Samples (1.0 ml) were electrophoresed on 8-25% gradient gels (Pharmacia #51-7066-00-02) using native buffer strips (Pharmacia #17-0517-01). Prior to electrophoresis, samples were heated for 20 minutes at 60° C. to inactivate any temperature sensitive proteases. Following electrophoresis, the gel was overlayed with a molten solution containing 10% Bacto-Skim Milk, 0.7% agarose and 0.01 M HEPES buffer (pH 7.2). The overlay was allowed to solidify at room temperature then the gel was incubated several hours at 37° C. until zones of clearing in the overlay appeared above the position of neutral protease in the PAGE gel. As a control for the position of Vibrio neutral protease, a highly purified sample of neutral protease wa used. The results of this experiment demonstrate that the HB101/pVPH2 broth contains a protease activity which comigrates on PAGE gels with authentic purified *V. proteolyticus* neutral protease. No such activity was found in broths of the control HB101/pBR322.

D. DNA Sequence of the DNA fragment encoding *V. proteolyticus* neutral protease — The *V. proteolyticus* neutral protease gene was sequenced by standard DNA sequencing protocols. This sequence is shown in FIGURE I. An open reading frame exists from approximately base #249-2078, within which the DNA region encoding the V. proteolyticus neutral protease is found.

EXAMPLE III

Cloning of *Bacillus stearothermophilus* B-3880 Neutral Protease)

The neutral protease of *Bacillus stearothermophilus* NRRL-B-3880 is described in U.S. Pat. No. 3,796,635. This neutral protease was cloned into E. coli HB101 in a manner analogous to that described in Example I. Chromosomal DNA was extracted from the organism and purified. The DNA was digested with Sau 3A under optimized conditions, then ligated to the cosmid vector pHC79 and packaged into bacteriophage lambda particles. *E. coli* HB101 was transfected with these recombinant phage, then the organisms were spread onto YET-Skim Milk Agar plates containing 50 μgm/ml ampicillin. Recombinant, protease-producing clones were surrounded by zones of clearing following 48 hours incubation at 37° C. One of these clones was selected for further study. It was shown to produce a neutral protease with the same molecular weight as thermolysin, the *Bacillus thermoproteolyticus* extracellular neutral protease, as determined by SDS-PAGE gels.

The cosmid containing the *B. stearothermophilus* neutral protease gene was isolated from the selected clone, and, in a manner similar to that described in Example II, the *Bacillus* neutral protease gene was subcloned. A 5.8 kb Eco RI fragment from the original cosmid clone was ligated to EcoRI-digested pBR322 to form a plasmid, designated pBSE1. This plasmid was transformed into *E. coli* HB101. The resulting HB101/pBSE1 colonies were surrounded by zones of clearing on skim-milk agar plates. A viable culture of the strain HB101/pBSE1 has been irrevocably deposited with ATCC and given the accession number ATCC 67500. All restrictions as to the availability of this strain to the public will be irrevocably removed upon the granting of a patent of which this strain is a subject.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

We claim:

1. An *E. coli* host cell transformed with the plasmid pBSE1 of ATCC 67500, which encodes the functional neutral protease isolated from *Bacillus stearothermophilus* NRRL-B-3880, wherein said *E. coli* expresses an active, functional neutral protease enzyme which exhibits activity in a milk clearing assay.

2. The *E. coli* of claim 1 which is *E. coli* ATCC 67500.

* * * * *